United States Patent
Nagel et al.

(10) Patent No.: US 10,261,035 B2
(45) Date of Patent: Apr. 16, 2019

(54) INDUCTIVE CONDUCTIVITY SENSOR AND METHOD

(71) Applicant: Endress+Hauser Conducta GmbH+Co. KG, Gerlingen (DE)

(72) Inventors: Thomas Nagel, Dresden (DE); André Pfeifer, Schkopau (DE); Christian Fanselow, Geringswalde (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 15/170,436

(22) Filed: Jun. 1, 2016

(65) Prior Publication Data

US 2016/0356736 A1    Dec. 8, 2016

(30) Foreign Application Priority Data

Jun. 1, 2015    (DE) .................. 10 2015 108 613

(51) Int. Cl.
| | |
|---|---|
| *G01R 27/08* | (2006.01) |
| *G01N 27/02* | (2006.01) |
| *G01N 27/08* | (2006.01) |

(52) U.S. Cl.
CPC ........... *G01N 27/025* (2013.01); *G01N 27/08* (2013.01)

(58) Field of Classification Search
CPC ...... G01N 27/025; G01N 27/08; G01N 27/07; G01N 27/06; G01N 27/02; G01N 27/023; G01R 27/22; G01R 27/28
See application file for complete search history.

(56) References Cited

U.S. PATENT DOCUMENTS

| | | | | | |
|---|---|---|---|---|---|
| 4,255,975 | A | * | 3/1981 | Debreuille | ............. E21B 47/00 33/313 |
| 5,077,525 | A | * | 12/1991 | West | ................... G01N 27/023 324/204 |

(Continued)

FOREIGN PATENT DOCUMENTS

| | | |
|---|---|---|
| DE | 102006025098 A1 | 11/2007 |
| DE | 102006025194 A1 | 12/2007 |

(Continued)

OTHER PUBLICATIONS

Search Report for German Patent Application No. 102015108613.1, German Patent Office, dated Oct. 7, 2015, 5 pp.

*Primary Examiner* — Thang X Le
(74) *Attorney, Agent, or Firm* — Mark A. Logan; PatServe

(57) ABSTRACT

The disclosure includes an inductive conductivity sensor for measuring the specific electrical conductivity of a medium with a transmitter coil energized by an input signal, a receiver coil coupled with the transmitter coil via the medium, which receiver coil supplies an output signal that is a measure for the conductivity of the medium, and a housing enclosing the transmitter coil and the receiver coil, which housing comprises at least one housing section designed to be immersed in the medium, the housing wall of said housing section surrounding the transmitter coil and the receiver coil. The housing is made of a magnetic plastic or resin for inductively decoupling the transmitter coil from the receiver coil. In certain embodiments, the housing may be made of a ferromagnetic material. Another aspect of the disclosure includes a method for manufacturing the conductivity sensor.

12 Claims, 4 Drawing Sheets

(56) References Cited

U.S. PATENT DOCUMENTS

| | | | | |
|---|---|---|---|---|
| 5,157,332 | A | * | 10/1992 | Reese .................. G01N 27/023 324/204 |
| 5,793,214 | A | * | 8/1998 | Wakamatsu ......... G01N 27/023 324/127 |
| 6,414,493 | B1 | * | 7/2002 | Rezvani ............... G01N 27/023 324/442 |
| 9,528,955 | B2 | * | 12/2016 | Pechstein ................ G01N 27/06 |
| 2009/0278528 | A1 | * | 11/2009 | Partsch ................ G01N 27/023 324/204 |
| 2011/0163756 | A1 | * | 7/2011 | Wang .................. G01N 27/023 324/537 |
| 2012/0326711 | A1 | * | 12/2012 | Roper ................. G01N 27/025 324/252 |
| 2014/0012238 | A1 | * | 1/2014 | Chen .................... A61B 17/068 606/1 |
| 2014/0167790 | A1 | * | 6/2014 | Pechstein ............. G01N 27/025 324/691 |
| 2015/0226683 | A1 | * | 8/2015 | Feldman ............... A01J 5/0133 324/640 |

FOREIGN PATENT DOCUMENTS

| | | |
|---|---|---|
| DE | 102007012335 A1 | 9/2008 |
| DE | 112007001875 T5 | 6/2009 |
| DE | 102008037893 A1 | 2/2010 |
| JP | 2000171534 A | 6/2000 |

\* cited by examiner

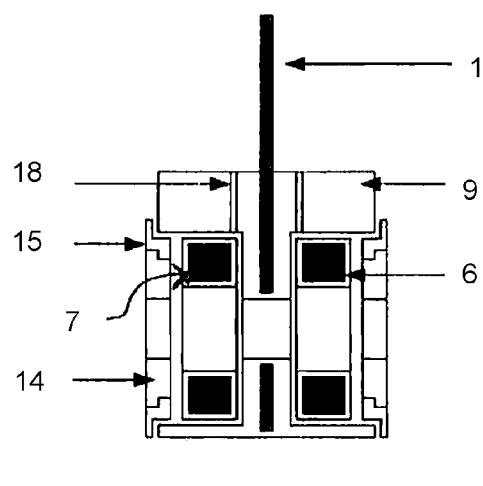
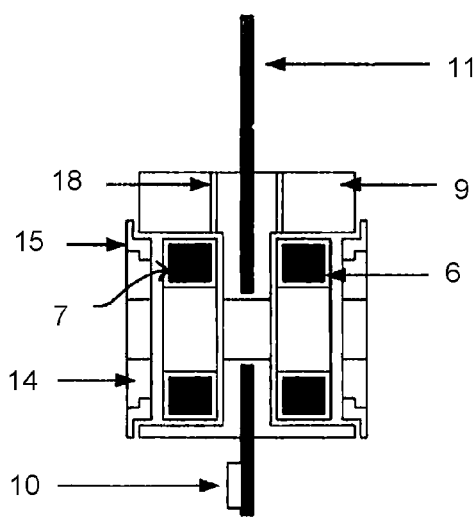
FIG. 2A  FIG. 2B

INDUCTIVE CONDUCTIVITY SENSOR AND METHOD

CROSS-REFERENCE TO RELATED APPLICATIONS

The present application is related to and claims the priority benefit of German Patent Application No. 10 2015 108 613.1, filed on Jun. 1, 2015, the entire contents of which are incorporated herein by reference.

TECHNICAL FIELD

The present disclosure relates to an inductive conductivity sensor for measuring the specific electrical conductivity of a medium and to a method for the production of the same.

BACKGROUND

The measurement of the specific electrical conductivity is used for controlling process engineering processes. In food technology, for example, product streams in pipes are differentiated from cleaning solutions or rinsing water by means of the measurement of the specific electrical conductivity. Depending upon certain media, process engineering processes are also influenced.

In general, conductivity sensors that work according to an inductive or a conductive measurement principle are often used in the process automation to measure the electrical conductivity of a medium. A conductive conductivity sensor comprises at least two electrodes that are immersed in a medium in order to take measurements. In order to determine the electrical conductivity of the medium, the resistance or conductance of the electrode measuring path in the medium is determined. If the cell constant is known, the conductivity of the medium can then be determined. In order to measure the conductivity of a measuring fluid by means of a conductive conductivity sensor, it is absolutely necessary that at least two electrodes come into contact with the measuring fluid.

With the inductive principle of determining the conductivity of process media, sensors are used that comprise both a transmitter coil and a receiver coil arranged at a distance from the transmitter coil. By means of the transmitter coil, an alternating electromagnetic field is produced, which affects charged particles, e.g., ions, in the liquid medium and generates a corresponding electric current in the medium. As a result of this electric current, an electromagnetic field is generated at the receiver coil, inducing a received signal (induction voltage) in the receiver coil according to Faraday's law of induction. This received signal can be analyzed and used to determine the electrical conductivity of the liquid medium.

Inductive conductivity sensors are typically designed as follows. The transmitter coil and the receiver coil are generally built as toroidal coils and comprise a continuous opening through which the medium can flow. The coils are arranged in a housing which is immersed in the medium to be measured. The medium thus flows around both coils. The excitation of the transmitter coil creates in the medium a closed current path that passes through both the transmitter coil and the receiver coil. By analyzing the current and voltage signals of the receiver coil in response to the signal from the transmitter coil, the conductivity of the measuring fluid can be determined. The principle in itself is established in industrial process measurement technology and has been documented in a large number of texts in the patent literature.

The coils consist of at least one winding of a conductor made of a wire that is wound on a coil carrier and provided with a magnetic core. The winding arrangement and winding form, the diameter of the wire, the winding material, and the core material define the value of the respective inductance and additional (quality) characteristics of the coil.

High-quality coils and cores are often used for conductivity sensors. These coils have a low temperature dependency because the relative permeability of the coils or the cores exhibits a low temperature dependency. Even in cores of very high quality, however, a certain temperature dependency exists, whether because of slow drift due to aging or at high temperatures, e.g., above 130° C. Relative permeabilities that change over time or with the temperature affect the measured value and thus the measured conductivity.

Often, conductivity sensors have additional functions that are also performed based upon alternating electromagnetic fields. For example, measurements of the flow rate, the pressure, or the density should be mentioned here. These additional functions can, however, only be performed one after the other because the magnetic and electrical fields influence one another.

BRIEF SUMMARY

At least one aspect of the present disclosure includes an inductive conductivity sensor for measuring the specific electrical conductivity of a medium with a transmitter coil energized by an input signal, and a receiver coil coupled with the transmitter coil via the medium. The receiver coil supplies an output signal that is a measure for the conductivity of the medium. A housing encloses the transmitter coil and the receiver coil, and the housing includes at least one housing section designed to be immersed in the medium. A housing wall of the housing section surrounds the transmitter coil and the receiver coil. The housing includes a magnetic—especially a ferromagnetic—plastic or resin inductively decoupling the transmitter coil from the receiver coil. The housing is surrounded by or insert-molded with a plastic that is different from the magnetic plastic. The inductive sensor further includes a circuit board with conductor paths and an extensive ground plane, where the ground plane is designed to capacitively decouple the transmitter coil and the receiver coil from the conductor paths. The circuit board is arranged between the transmitter coil and the receiver coil, and the transmitter coil and the receiver coil are in contact with the circuit board. The circuit board includes a temperature sensor which is arranged outside of the housing.

The inductive conductivity sensor also includes at least one cover made of a magnetic, especially a ferromagnetic, plastic or resin, where the cover closes the transmitter coil and/or the receiver coil. In certain embodiments, the inductive conductivity sensor includes additional sensors—in particular, pressure sensors and flow rate sensors—and the housing has recesses for these additional sensors.

Another aspect of the disclosure includes a method for manufacturing the conductivity sensor disclosed herein using the following steps: manufacturing a housing made of a magnetic, in particular a ferromagnetic, plastic or resin; mounting at least one transmitter coil and one receiver coil in the housing; insert-molding the housing with an additional plastic that is different from the magnetic plastic; and arranging the transmitter coil and the receiver coil on a circuit board; and insert-molding the circuit board.

BRIEF DESCRIPTION OF THE DRAWINGS

FIGS. 2A and 2B show cross-sectional views of a housing of a conductivity sensor according to exemplary embodiments of the present disclosure.

In the Figures, the same features are marked with the same reference symbols.

DETAILED DESCRIPTION

Figure 1:
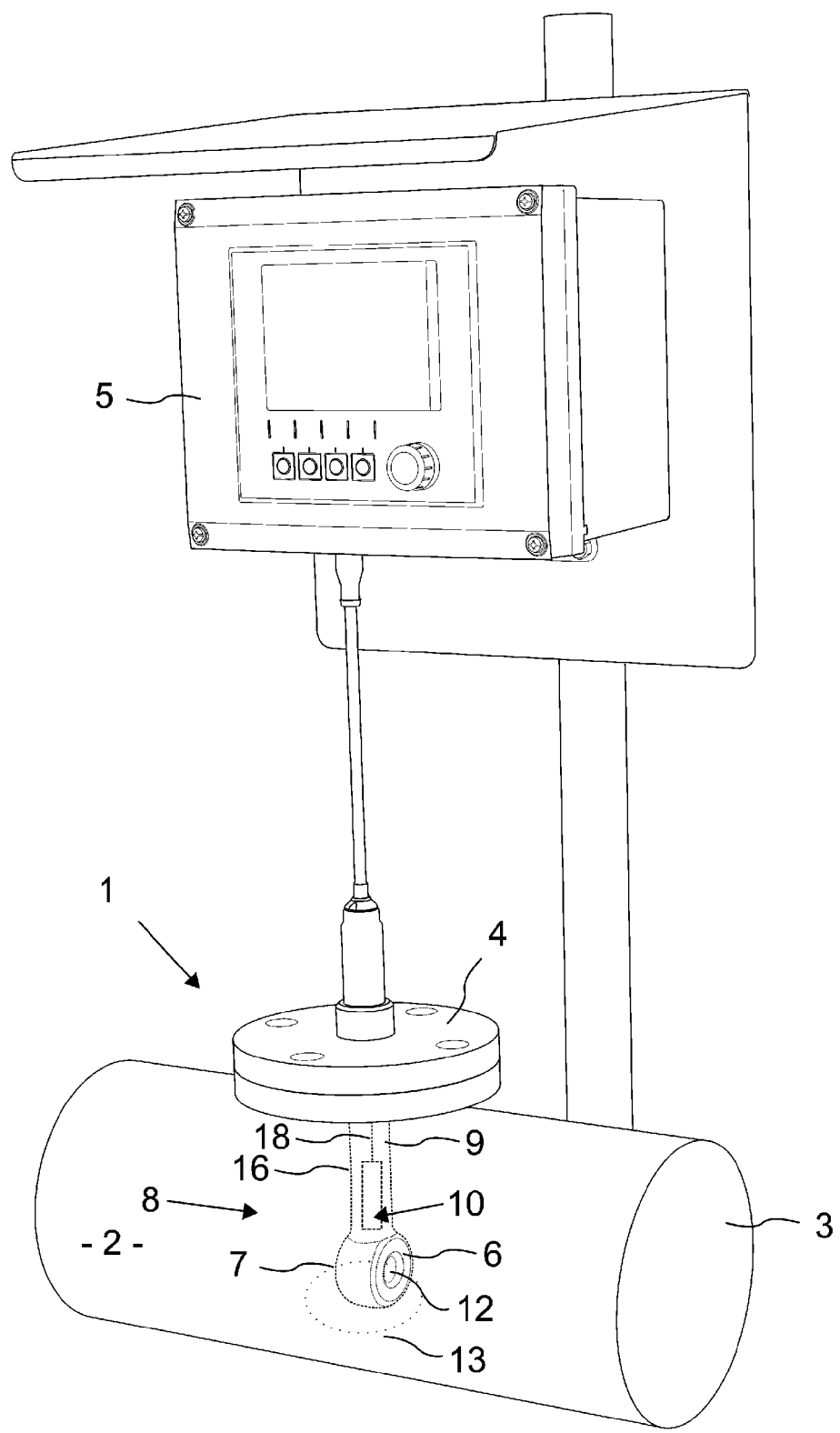
FIG. 1 shows a conductivity sensor according to exemplary embodiments of the present disclosure.

The present disclosure provides an adaptable conductivity sensor that takes measurements in a manner that is stable in the long term and with respect to the temperature. The present disclosure includes an inductive conductivity sensor characterized in that its housing comprises a magnetic plastic or resin for inductively decoupling the transmitter coil from the receiver coil. In certain embodiments, the plastic or resin material may be a ferromagnetic material. Thus, an inductive decoupling of the coils from one another occurs. The coupling between the two coils is an unwanted component of the measured value. In order to determine the measured value correctly, this coupling must be determined and reconciled against the measured value, i.e., reduced. Since the coupling essentially depends upon the relative permeability, and since the latter is, as mentioned, temperature dependent, the temperature dependency of the conductivity sensor can be reduced by decoupling the coils from one another.

In food processing technology and biotechnology, there are requirements that the sensors are able to be sterilized thermally and designed to be cleaned well (i.e., hygienic design). As a matter of principle, inductive conductivity sensors must at least in part consist of an electrical insulating material. Plastic is generally used for this purpose. These plastics require a special approval for use in the area of food technology and biotechnology.

In one advantageous embodiment, the housing is therefore surrounded by a plastic that is different from the magnetic plastic. In certain embodiments, the magnetic portion of the housing may be insert-molded with the different material.

In order to reduce the capacitive coupling, the conductivity sensor comprises a circuit board with conductor paths and an extensive ground plane, wherein the ground plane is designed for this capacitive decoupling of the transmitter coil and the receiver coil from the conductor paths, wherein the circuit board is arranged between the transmitter coil and the receiver coil, and the transmitter coil and the receiver coil are in contact with the circuit board. The circuit board may include a temperature sensor that is arranged outside the housing.

In one advantageous further development, the conductivity sensor comprises at least one cover made of a magnetic—in particular, ferromagnetic—plastic or resin, wherein the cover closes the transmitter coil and/or the receiver coil. The cover further reduces the stray field of the coils. The cover comprises a non-conducting ring, wherein the small non-conducting ring prevents a short circuit between turns of the coils from occurring. At the same time, this cover serves as protection against mechanical influences.

In one preferred embodiment, the conductivity sensor comprises additional sensors—in particular, pressure sensors and flow rate sensors—and the housing comprises recesses for these additional sensors. As a result of the magnetic as well as, if applicable, capacitive decoupling, measurements can be taken by the additional sensors at the same time and without interference.

The present disclosure further includes a method for the production of a conductivity sensor as described above, comprising the following steps: Manufacturing a housing made of a magnetic—in particular, ferromagnetic—plastic or resin; mounting at least one transmitter coil and one receiver coil in the housing; and insert-molding the housing with a plastic that is different from the magnetic plastic. In at least on embodiment, the transmitter coil and the receiver coil are arranged on a circuit board, and the circuit board is insert-molded with plastic.

For the purposes of promoting an understanding of the principles of the present disclosure, reference will now be made to the embodiments illustrated in the drawings, and specific language will be used to describe the same. It will nevertheless be understood that no limitation of the scope of this disclosure is intended, with any additional alterations, modifications, and further applications of the principles of this disclosure being contemplated hereby as would normally occur to one skilled in the art. Accordingly, this disclosure is intended to cover alternatives, modifications, and equivalents as may be included within the spirit and scope of this disclosure as defined by the appended claims. While this technology may be illustrated and described in a preferred embodiment, the systems, methods, and techniques hereof may comprise many different configurations, forms, materials, and accessories.

An inductive conductivity sensor 1 according to at least one embodiment of the present disclosure is shown in FIG. 1. The conductivity sensor 1 may be use in process automation. The conductivity sensor 1 may be arranged—for example, via a flange 4 (generally via a process connection)—on a vessel 3 in which the medium 2 to be measured is located. The vessel 3 may be a pipe made, for example, of plastic or metal.

The conductivity sensor 1 comprises a transmitter coil 6 and a receiver coil 7 that are located inside a housing 9. The housing 9 comprises a housing wall 16. The housing 9 is manufactured from a plastic—in particular, a thermoplastic. In certain embodiments, the plastic may be one approved for use in the area of food technology and biotechnology. For example, the plastic may be a polyaryl ether ketone such as polyetheretherketone (PEEK) as described further below.

The transmitter coil 6 and the receiver coil 7 are arranged, for example, opposite one another on sides of a circuit board (not shown) that face away from one another. In this way, the transmitter coil 6 and receiver coil 7, which are designed as rotation-symmetric toroidal coils ("toroids"), are arranged coaxially, one behind the other. The circuit board comprises the conductor paths that contact the coils and connect the transmitter coil 6 with a driver circuit, and the receiver coil 7 with a receiver circuit. The driver circuit and the receiver circuit can form part of the sensor circuit installed on the circuit board. The coils 6, 7 are connected with a data processing unit 5 in FIG. 1, with a measuring transducer.

The housing 9 forms a channel 12 that passes through the transmitter coil 6 and the receiver coil 7 along their axes of rotation. If the housing 9 is immersed in an electrically conductive medium 2, the medium surrounds the housing 9 or a housing section 8 designed to be immersed in the medium 2 and enters the channel 12, so that, in the medium, a closed current path 13 passing through both coils 6, 7 can form when the transmitter coil 6 is excited or flowed through by an input signal, i.e., an alternating voltage.

The conductivity sensor functions in the manner of a double transformer, wherein the transmitter and the receiver coils 6, 7 are inserted as mentioned into the medium 2 to at least the extent that a closed current path 13 running through the medium 2 and passing through the transmitter and the receiver coils 6, 7 can be formed. When the transmitter coil 6 is excited with an alternating voltage signal used as an input signal, it generates a magnetic field which induces a current path 13 which passes through the coils 6 and 7 and the strength of which depends upon the electrical conductivity of the medium 2. Thus, a current path with an ionic conduction results in the medium 2. Since this alternating electrical current in the medium in turn generates a varying magnetic field that surrounds it, an alternating current is induced in the receiver coil 7 as an output signal. This alternating current and the corresponding alternating voltage respectively, which are delivered by the receiver coil 7 as output signal, are a measure of the electrical conductivity of the medium 2.

The conductivity sensor 1 comprises a temperature sensor 10 for measuring the temperature of the medium 2. The data processing unit 5 determines the conductivity of the medium 2 based upon the input signal, the output signal, and the temperature of the medium 2.

The temperature sensor 10 is an electrical or electronic component that supplies an electrical signal as a measure for the temperature. The component is, for example, a negative temperature coefficient thermistor (NTC thermistor) or a positive temperature coefficient thermistor (PTC thermistor), the resistance of which changes with the temperature. Examples in this regard are platinum measuring resistors or ceramic PTC thermistors. Alternatively, a component may be used that directly supplies a processable electrical signal, such as, for example, a semiconductor temperature sensor that supplies a current or voltage proportional to the temperature. As additional alternatives, a thermocouple or other common temperature measuring element may be used.

The temperature sensor 10 comprises a temperature element that supplies an electrical signal as a measure for the temperature. This is, for example, a thermistor, such as a Pt100 or Pt1000. Via wires 18, this signal—such as, for example, resistance values or a voltage—is transmitted to the measuring transducer 5.

FIGS. 2A and 2B shows a cross section of the housing 9 of the conductivity sensor 1. The housing 9 comprises a magnetic—in particular, ferromagnetic—plastic or a magnetic—in particular, ferromagnetic—resin for inductively decoupling the transmitter coil 6 from the receiver coil 7. Examples of magnetic plastics are Luvocom 1105-9096, Ferrotron®, or Fluxtrol®. The magnetic material is used to inductively decouple the coils 6, 7 from one another; see also FIG. 3B. The magnetic resin includes resin mixtures with magnetic filler materials. A cold manufacturing method is thus possible, whereby the magnetic filler materials better maintain their magnetic properties. Resins are also easily insert-molded (see below).

The housing 9 is surrounded by a plastic that is different from the magnetic plastic. In one embodiment, the housing is insert-molded. The manufacturing method for the conductivity sensor 1 is then as follows: manufacturing the housing 9, mounting at least one transmitter coil 6 and one receiver coil 7 in the housing 9, and insert-molding the housing 9 with the plastic that is different from the magnetic plastic.

The housing 9 may be designed as a milled part or an injection part, as a complete carrier, or as a plug-in unit made of several parts. In one embodiment, in case of an injection part or a plug-in part, a circuit board 11 may be placed between the coils 6, 7 as an insert that is insert-molded with them. The circuit board 11 may be a star or flex circuit board. The coils 6 and 7 are in contact with the circuit board 11. For this purpose, the circuit board 11 comprises conductor paths (not shown) for connecting the coils 6 and 7 with the already mentioned measuring transducer 5. The circuit board 11 comprises a large ground plane 17. This ground plane 17 reduces the capacitive coupling of the coils 6 and 7 with the conductor paths on the circuit board 11.

The coils 6, 7 are covered by a cover 14. With the exception of a small non-conducting ring 15, this cover 14 consists of the already discussed magnetic plastic or magnetic resin. The cover 14 further reduces the stray field of the coils 6, 7. The non-conducting ring 15 prevents a short circuit between turns of the coils 6, 7. At the same time, this cover 14 serves as protection against mechanical influences.

In FIG. 2B, the circuit board 11 is extended downward and equipped with the temperature sensor 10; i.e., the temperature sensor 10 is positioned outside the housing 9 in this embodiment. Provided with a protecting cap, the temperature sensor may also be insert-molded later.

Figure 3A:
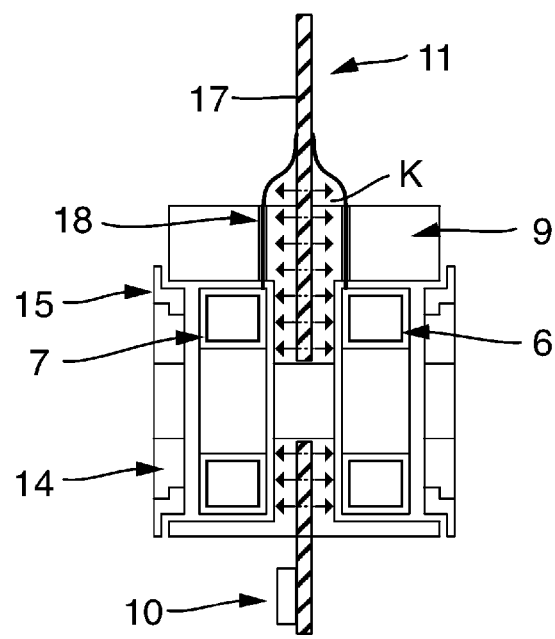
FIG. 3A shows an inductive coupling of a conductivity sensor housing according to exemplary embodiments of the present disclosure.

FIG. 3A shows the capacitive decoupling. The circuit board 11 interrupts the capacitive coupling K, illustrated by arrows. The interruption is illustrated with dashed lines. The capacitive coupling between the coils 6 and 7 and the conductor paths of the circuit board 11 is reduced by the grounded, largely mounted, ground plane 17 of the injected or embedded circuit board 11.

Figure 3B:
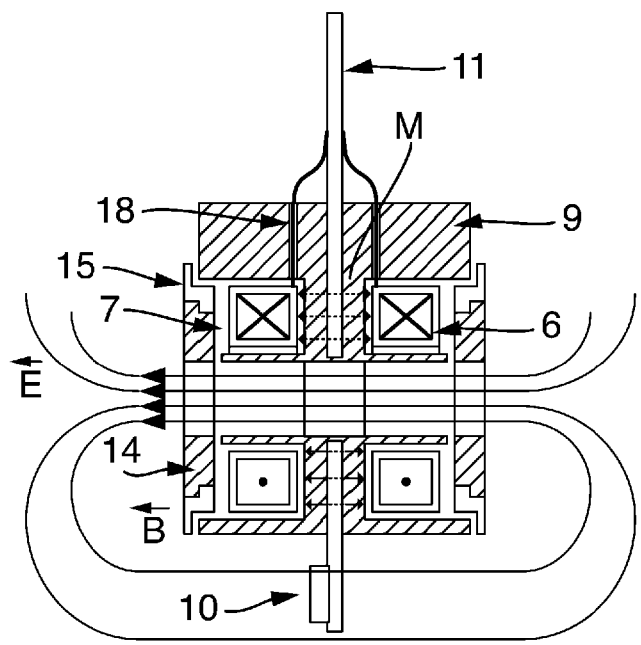
FIG. 3B shows a capacitive coupling of a conductivity sensor housing according to exemplary embodiments of the present disclosure.

FIG. 3B shows the inductive decoupling. The inductive coupling M, illustrated by arrows, is interrupted by means of the magnetic material of the housing 9. The interruption is illustrated with dashed lines. Stray fields which occur are absorbed by the magnetic housing 9.

Figure 4:
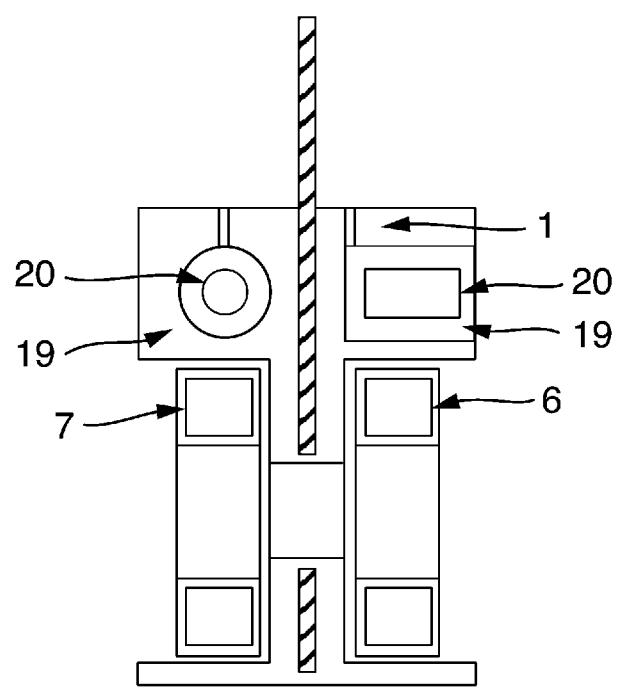
FIG. 4 shows a conductivity sensor according to exemplary embodiments of the present disclosure.

In conductivity sensors with additional integrated functions, measurements can be performed only one after the other, since the magnetic and electric fields influence one another. For this reason, in FIG. 4, various sensor elements are integrated into a common housing and magnetically and capacitively shielded as described above. In an inductive conductivity sensor 1 comprising a housing 9 consisting of a magnetic plastic or resin, recesses 19 for additional sensors 20—for example, inductive sensors or sensors that function according to other principles—are applied at any positions in the same housing 9, in addition to the usual coils 6, 7. These recesses 19 may comprise, for example, magnetic flow rate sensors, pressure sensors, or other sensors. The magnetic plastic prevents mutual interactions between the inductive coils 6, 7 and the various additional sensors 20. The contact is also established via wires 18—for example, in conduits—up to the circuit board 11. The additional sensors 20 are also hygienically insert-molded by a plastic other than the magnetic plastic.

While various embodiments of a inductive conductivity sensor and methods of making the same according to the present disclosure have been described as having an illustrative design, the present disclosure may be further modified within the spirit and scope of this disclosure. The present application is therefore intended to cover any variations, uses, or adaptations of the invention using its general principles. Further, the present application is intended to cover such departures from the present disclosure as come within known or customary practice in the art to which this invention pertains.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. An inductive conductivity sensor for measuring the specific electrical conductivity of a medium, the sensor comprising:
   a transmitter coil energized by an input signal;
   a receiver coil, the receiver coil coupled with the transmitter coil via the medium, wherein in response to the input signal the receiver coil generates an output signal that is a measure for the conductivity of the medium; and
   a housing, the housing enclosing the transmitter coil and the receiver coil and the housing including a first portion comprising a magnetic plastic or resin material, wherein at least the first portion of the housing is sealed from intrusion by the medium, and
   wherein the transmitter coil and the receiver coil are arranged within the housing such that the transmitter coil and the receiver coil are inductively decoupled by the first portion of the housing.

2. The sensor of claim 1, wherein the magnetic plastic or resin material is a ferromagnetic plastic or resin material.

3. The sensor of claim 1, wherein the housing includes a second portion comprising a plastic or resin material that is different from the plastic or the resin of the first portion.

4. The sensor of claim 3, wherein the second housing portion is insert-molded at least partially around the first portion.

5. The sensor of claim 1, further comprising a circuit board with conductor paths and a ground plane, the circuit board disposed between the transmitter coil and the receiver coil such that the ground plane capacitively decouples the transmitter coil and the receiver coil, wherein the transmitter coil and the receiver coil are in electrical contact with the circuit board.

6. The sensor of claim 3, further comprising a circuit board with conductor paths and a ground plane, the circuit board disposed between the transmitter coil and the receiver coil such that the ground plane capacitively decouples the transmitter coil and the receiver coil, wherein the transmitter coil and the receiver coil are in electrical contact with the circuit board.

7. The sensor of claim 5, further comprising a temperature sensor.

8. The sensor of claim 7, wherein the temperature sensor is disposed outside the housing.

9. The sensor of claim 8, wherein the circuit board extends from the housing and the temperature sensor is connected to the circuit board.

10. The sensor of claim 1, further comprising at least one cover made of a magnetic plastic or resin material, wherein the at least one cover caps the housing adjacent transmitter coil and/or the receiver coil.

11. The sensor of claim 10, wherein the magnetic plastic or resin material is a ferromagnetic plastic or resin material.

12. The sensor of claim 1, wherein the sensor includes pressure and/or flow rate sensors, and the housing includes recesses for the pressure and/or flow rate sensors.

\* \* \* \* \*